United States Patent
Yang et al.

(10) Patent No.: US 12,146,132 B2
(45) Date of Patent: Nov. 19, 2024

(54) **GENETICALLY MODIFIED *ZYMOMONAS MOBILIS* TO UTILIZE INORGANIC N SOURCE, METHODS AND USES THEREOF**

(71) Applicant: Hubei University, Wuhan (CN)

(72) Inventors: Shihui Yang, Wuhan (CN); Mimi Hu, Wuhan (CN); Qiaoning He, Wuhan (CN)

(73) Assignee: Hubei University, Wuhan (CN)

( * ) Notice: Subject to any disclaimer, the term of this patent is extended or adjusted under 35 U.S.C. 154(b) by 0 days.

(21) Appl. No.: 18/626,055

(22) Filed: Apr. 3, 2024

(65) Prior Publication Data
US 2024/0352403 A1  Oct. 24, 2024

(30) Foreign Application Priority Data
Apr. 24, 2023 (CN) .......................... 202310447119.2

(51) Int. Cl.
| | | |
|---|---|---|
| *C12N 1/20* | (2006.01) | |
| *C12P 7/06* | (2006.01) | |
| *C12P 7/16* | (2006.01) | |
| *C12P 7/42* | (2006.01) | |
| *C12R 1/01* | (2006.01) | |

(52) U.S. Cl.
CPC .............. *C12N 1/205* (2021.05); *C12P 7/065* (2013.01); *C12P 7/16* (2013.01); *C12P 7/42* (2013.01); *C12R 2001/01* (2021.05)

(58) Field of Classification Search
CPC .. C12N 1/205; C12P 7/065; C12P 7/16; C12P 7/42; C12R 2001/01
See application file for complete search history.

(56) References Cited

U.S. PATENT DOCUMENTS 8,865,440 B2 * 10/2014 Brown .................... C12P 7/065
435/165

FOREIGN PATENT DOCUMENTS

| CN | 108300732 A | 7/2018 |
| CN | 110358767 A | 10/2019 |
| CN | 110408642 A | 11/2019 |

OTHER PUBLICATIONS

Title of the Item: Genbank CP023715.1 Publication Date: Jul. 7, 2020 Name of the Author: Yang, s. et al. Article Title: Zymomonas mobilis subsp. mobilis ZM4=ATCC 31821 chromosome, complete genome Pages: Base sequence 104521-106158.

* cited by examiner

*Primary Examiner* — Aaron J Kosar
(74) *Attorney, Agent, or Firm* — Nitin Kaushik

(57) ABSTRACT

Genetically modified *Zymomonas mobilis* to utilize inorganic N source, methods and uses thereof are provided. The genetically modified *Z. mobilis* has a genome with the knockout of a locus ZMO1107 from *Z. mobilis* ZM4 could ferment inorganic N source.

1 Claim, 11 Drawing Sheets

Specification includes a Sequence Listing.

GENETICALLY MODIFIED *ZYMOMONAS MOBILIS* TO UTILIZE INORGANIC N SOURCE, METHODS AND USES THEREOF

CROSS-REFERENCE TO RELATED APPLICATIONS

This disclosure claims priority to Chinese Patent Application NO:202310447119.2, filed with China Intellectual Property Office on Apr. 24, 2023, the entire contents of which are incorporated herein by reference.

SEQUENCE LISTING

The sequence listing xml file submitted herewith, named "Sequence_Listing.xml", created on Mar. 29, 2024, and having a file size of 23,250 bytes, is incorporated by reference herein.

TECHNICAL FIELD

This disclosure relates to *Zymomonas mobilis*. Specifically, this disclosure relates to genetically modified *Z. mobilis* to utilize inorganic N source (e.g., nitrogen gas), methods and uses thereof.

BACKGROUND

The statements herein provide background information relevant to the present disclosure only and do not necessarily constitute prior art.

As a facultative anaerobic Gram-negative bacterium, *Z. mobilis* has many unique physiological and excellent industrial characteristics, such as few byproducts, high specific productivity, high specific rate of sugar utilization, high ethanol tolerance. And, *Z. mobilis* could decouple its growth and energy consumption, does not require controlled aeration and not be infected by phages during fermentation, and it is generally regarded as safe (GRAS). In addition, *Z. mobilis* has been reported to utilize nitrogen gas as a sole N source to produce ethanol without compromising its final ethanol yield. Specifically, *Z. mobilis* ZM4 could produce ethanol with a yield of 97% of its theoretical yield, which is higher than its maximum theoretical conversion (94%) when using 1% corn steep liquor as the N source. However, due to the stringent regulation, the capacity of N fixation in *Z. mobilis* ZM4 for industrialization is limited. Therefore, it is desirable to further understand the nitrogen regulation to help release the capacity of N fixation, and make *Z. mobilis* an industrial strain that could efficiently utilize nitrogen gas for fermentation.

SUMMARY

In a first aspect, embodiments disclose a genetically modified strain of *Zymomonas mobilis*. The genetically modified strain has a genome with the knockout of locus ZMO1107 from *Z. mobilis* ZM4. *Z. mobilis* ZM4 is the strain of *Z. mobilis* subsp. *mobilis* ZM4 (ATCC 31821). The ZMO1107 encodes feast/famine response regulatory protein or leucine response regulatory protein. And the gene of ZMO1107 is also named lrp, and its gene ID is 58026885.

In a second aspect, embodiments disclose a gene from *Z. mobilis*. The gene encodes feast/famine response regulatory protein or leucine response regulatory protein, and regulates nitrogen metabolism. The gene's locus of genome of the ZM4 is ZMO1107. The gene also named lrp, and its gene ID is 58026885.

In a third aspect, embodiments disclose a method for fermenting an inorganic N source with a genetically modified strain of *Z. mobilis*. The method includes inoculating the genetically modified strain of *Z. mobilis* into a medium with containing the inorganic N source to ferment. The inorganic N source is selected from at least one of nitrogen gas and ammonium sulfate. The genetically modified strain of *Z. mobilis* has a genome with the knockout of locus ZMO1107 from *Z. mobilis* ZM4. *Z. mobilis* ZM4 is the strain of *Z. mobilis* subsp. *mobilis* ZM4 (ATCC 31821). The ZMO1107 encodes feast/famine response regulatory protein or leucine response regulatory protein. And the gene of ZMO1107 is also named lrp, and its gene ID is 58026885.

In a fourth aspect, embodiments disclose a method for constructing of a genetically modified strain of *Z. mobilis*. The genetically modified strain of *Z. mobilis* has a genome with the knockout of locus ZMO1107 from *Z. mobilis* ZM4. *Z. mobilis* ZM4 is the strain of *Z. mobilis* subsp. *mobilis* ZM4 (ATCC 31821). The ZMO1107 encodes feast/famine response regulatory protein or leucine response regulatory protein. And the gene of ZMO1107 is also named lrp, and its gene ID is 58026885. The method includes: constructing an editing plasmid for knocking out the gene of lrp; and transferring the editing plasmid into the *Z. mobilis* ZM4.

In a fifth aspect, embodiments disclose uses of the genetically modified strain of *Z. mobilis* said in the first aspect. The uses include microbial N fixation, and fermentation with organic N source and/or inorganic N source.

DETAILED DESCRIPTION OF THE EMBODIMENTS

The inventors of this disclosure creatively found that a knockout of a locus named ZMO1107 of the genome from Z. mobilis ZM4 could significantly improve the ability to utilize inorganic N source, such as nitrogen gas and/or ammonium sulfate. And a genetically modified strain by the knockout has a higher growth rate and biomass than those of Z. mobilis ZM4. And the gene of ZMO1107 is also named lrp, and its gene ID is 58026885. In addition, this disclosure also discovers that the gene lrp is capable of inhibiting the expression of the gene of nifA that regulate the N fixation. And the ZMO1107 provides a target point of engineering strains of Z. mobilis for constructing N fixation and other industrial strains. Specifically, benefit by the endogenous I-F CRISPR-Cas editing system of ZM4, the locus of ZMO1107 could be knocked out.

Therefore, embodiments disclose a genetically modified strain of Z. mobilis. The genetically modified strain has a genome with the knockout of locus ZMO1107 from Z. mobilis ZM4. Z. mobilis ZM4 is the strain of Z. mobilis subsp. mobilis ZM4 (ATCC 31821). The ZMO1107 encodes feast/famine response regulatory protein or leucine response regulatory protein. And the gene of ZMO1107 is also named lrp, and its gene ID is 58026885.

In addition, embodiments disclose a method for fermenting an inorganic N source with a genetically modified strain of Z. mobilis. The method includes inoculating the genetically modified strain of Z. mobilis into a medium with containing the inorganic N source to ferment. The inorganic N source is selected from at least one of nitrogen gas and ammonium sulfate. The genetically modified strain of Z. mobilis has a genome with the knockout of locus ZMO1107 from Z. mobilis ZM4. Z. mobilis ZM4 is the strain of Z. mobilis subsp. mobilis ZM4(ATCC 31821). The ZMO1107 encodes feast/famine response regulatory protein or leucine response regulatory protein. And the gene of ZMO1107 is also named lrp, and its gene ID is 58026885.

In these embodiments, the genetically modified strain of Z. mobilis, that has been knocked out the gene lrp, is able to obtain biomass with an OD600 value of 0.9 in 30 h with ammonium sulfate as the sole N source.

In these embodiments, the genetically modified strain of Z. mobilis, that has been knocked out the gene lrp, is able to obtain biomass with an OD600 value of 1.8 in 30 h with ammonium sulfate and nitrogen gas as the N source.

In these embodiments, the genetically modified strain of Z. mobilis, that has been knocked out the gene lrp, is able to obtain biomass with an OD600 value of 0.6 at 30 h with nitrogen gas as the sole N source.

In addition, in some embodiments, the genetically modified strain of Z. mobilis, that has been knocked out the gene lrp, is able to use organic N source, such as yeast extract. And the genetically modified strain could obtain biomass with an OD600 value of 4.9 in 20 hours.

Figure 5A:
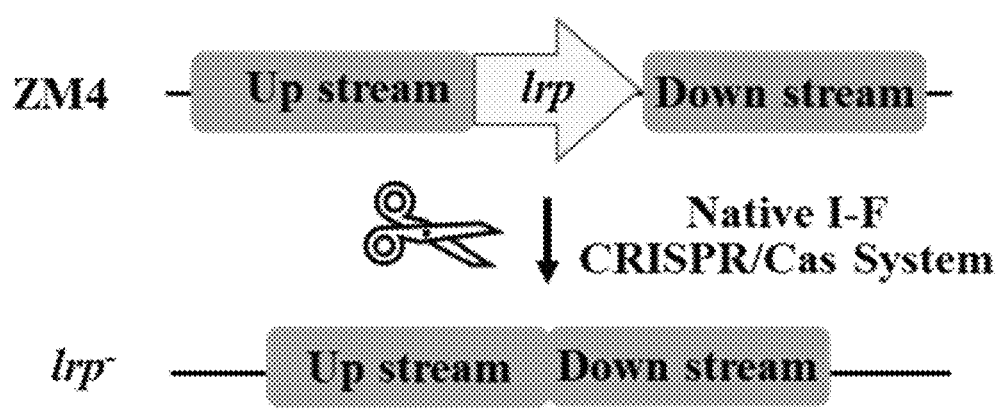
FIG. 5A illustrates the genome of ZM4 and the genome of lrp⁻ provided with embodiments.

As shown in FIG. 5A, embodiments also disclose a method for constructing of a genetically modified strain of Z. mobilis. The method includes the steps of constructing an editing plasmid for knocking out the gene of lrp, and transferring the editing plasmid into the Z. mobilis ZM4. Furthermore, the method further includes the steps of continuously culturing and passaging the ZM4 with the transferred editing plasmid in a non-resistant RM liquid culture medium, and obtaining the strain with the editing plasmid lost by verifying through colony PCR.

In some embodiments, the editing plasmid carries a leader shown in SEQ ID NO:1, two iterons shown in SEQ ID NO:2, a donor shown in SEQ ID NO:3 that locates upstream of the leader, and a guider shown in SEQ ID NO:4 between the two iterons. Therein, the guider targetedly bind to the locus of ZMO1107. By transferring the editing plasmid into ZM4, ZM4 could utilize its endogenous CRISPR-IF Cas enzyme and gRNAs transcribed from the guider to knock out the gene lrp.

In addition, embodiments also provide uses of the genetically modified strain of Z. mobilis. The uses include microbial N fixation, and fermentation with organic N source and/or inorganic N source to produce at least one of ethanol, 2,3-butanediol, isobutanol, poly-beta-hydroxybutyric acid (PHB) or lactic acid.

The procedure for constructing the editing plasmid used in the above embodiments, performing knockout of the gene lrp from ZM4 using the editing plasmid will be described below to obtain the genetically modified strain of Z. mobilis (named lrp⁻). And uses of lrp⁻ will be described in more detail.

1. Construct an Editing Plasmid for Knocking Out Lrp
(1) Guider

A sequence of 32 bp downstream of the CCC site of the PAM was selected as a guider from the gene lrp (Gene ID: 58026885), shown in SEQ ID NO:4.

(2) Construct a Targeting Plasmid

Primers (gRNA-lrp-F, shown in SEQ ID NO. 5; gRNA-lrp-R, shown in SEQ ID NO. 6) were synthesized based on the sequence of the guider.

In one embodiment, sequences of the primers were ligated to a base plasmid (named pEZ15Asp, CN110408642A) with carrying a expression unit of CRISPR-IF and a gene of spectinomycin. The process to construct the targeting plasmid specifically include: linearizing pEZ15Asp with restriction enzyme BsaI; annealing primers gRNA-lrp-F and/or gRNA-lrp-R; ligating the linearized pEZ15Asp with the annealed primers; transferring the ligated product into E. coli DH5α; screening positive colonies by colony PCR; and finally verifying by sequencing. Therein, 10 μM primers were denatured at 95° C. for 5 min and then cooled to room temperature for use in the annealing process.

Therein, pEZ15Asp has a first region of original replicon shown in SEQ ID NO:19, a second region of original replicon shown in SEQ ID NO:20 and a marker region (Spe gene) located between the first region of original replicon and the second region of original replicon. The first region of original replicon locate between 156 and 1069 bp. The second region of original replicon locates between 2142 and 3015 bp.

The pEZ15Asp could be constructed by inserting an initial CRISPR cluster on pEZ15A and replacing its second region of original replicon. Therein, pEZ15A could be constructed by the method according to "Yang S, mohaghaeghi A, franden M A, et al, Metabolic engineering of Zymomonas mobilis for 2,3-butanediol production from lignocellulosic biomass sugars [J]. Biotechnol Biofuels, 2016, 9(1):189". For obtaining pEZ15A with the different coding genes (e.g. resistance genes), reference could be made to "Construction and Application of Plasmid pUC19-CM-D [J]. Agricultural Science & Technology, 2010, 11(5): 31~33".

(3) Construct the Editing Plasmid

A upstream sequence from lrp (shown as SEQ ID NO:7) was amplified by a PCR with primers: up-lrp-F (shown as SEQ ID NO:8), and up-lrp-R (shown as SEQ ID NO:9).

A downstream sequence from lrp (shown as SEQ ID NO:10) was amplified by a PCR with primers: down-lrp-F (shown as SEQ ID NO:11), and down-lrp-R (shown as SEQ ID NO:12).

The targeting plasmid prepared in the previous step, was amplified by a PCR with primers pL2R-FK-F (shown as SEQ ID NO:13), and pL2R-FK-R (shown as SEQ ID NO:14). The PCR procedure was: pre-denaturation at 98° C. for 3 min; denaturation at 98° C. for 10 s, annealing at 55° C. for 10 s, extension at 72° C. (set according to fragment length for 10 s/kb for 30 cycles); and 72° C. for 5 min after the cyclic reaction. The upstream sequence from lrp, the downstream sequence from lrp and the targeting plasmid of product from the PCR were ligated by Gibson assembly. And its product was transferred into E. coli DH5a. For constructing the editing plasmid, the process also included screening positive colonies by colony PCR; and finally verifying by sequencing.

2. Construct lrp⁻

(1) Prepare Competent ZM4

100-μL frozen bacteria of ZM4 were inoculated in 1 mL RM from stock and cultivated at 30° C. After grown to the mid-exponential phase, the culture were then shifted into 200 mL fresh RM liquid medium in a 250 mL flask with the initial OD600 nm value of 0.025~0.03. When the OD600 nm value exceeded 0.3, the thalli from the culture were collected by centrifuging at room temperature, and washed once with sterile water and twice with 10% glycerol. The thalli of competent ZM4 were then slowly resuspended with 1-2 mL 10% glycerol, and divided 55 μL into a 1.5 mL EP tubes.

(2) Electro-Transfer 1 mg of the editing plasmid was added to a 1.5 mL EP tube with containing 55 μL of competent ZM4, gently mixed and shifted into a 1-mm electroporation cuvette. The electro-transformation produce was set as: 200Ω, capacitor: 25 μF, voltage: 1.6 KV. And 1 mL RM of liquid medium was added into the electroporation cuvette after electro-transferring, mixed well and then shifted to a sterile EP tube, sealed and incubated in a 30° C. thermostatic incubator for 4~6 h. And 100 μL of the solution of transferred strains was taken and spread evenly to a RM plate supplemented with 100 g/mL spectinomycin. The RM plates were sealed with sealer films and reversely placed in an incubator at 30° C.

(3) Colony PCR

After the colonies were grown on the RM plates, colony PCR was performed to validate the positive colonies. The colony PCR system and the PCR procedure are shown in Tables 1 and 2, respectively. The positive colonies were preserved with glycerol after activating in medium of RM+Spe.

TABLE 1

Reaction System of colony PCR

| Component | Dosage (μL) |
| --- | --- |
| F-primer (10 μM) | 0.4 |
| R-primer (10 μM) | 0.4 |

TABLE 1-continued

Reaction System of colony PCR

| Component | Dosage (μL) |
| --- | --- |
| 2 × T5 Super PCR Mix (Tsingke) | 5 |
| Template (single colony dissolved in 10 μL ddH₂O) | 1 |
| ddH₂O | 3.2 |
| Total volume | 10 |

TABLE 2

Procedure of colony PCR

| Temperature | Time | cycles |
| --- | --- | --- |
| 98° C. | 3 min | |
| 98° C. | 10 s | 29 |
| 55° C. | 10 s | |
| 72° C. | 10 s | |
| 72° C. | 3 min | |
| 16° C. | hold | |

(4) Eliminate the Editing Plasmid

The positive colonies were inoculated in a liquid medium of RM without antibiotics. 100 μL of bacterial liquid was shifted into 1 mL of fresh RM after the bacterial liquid grows to be cloudy. After 4-5 generations, 100 μL of bacterial liquid was diluted and plated on an flat plate of RM. After single colony grow out on the plate, colony PCR was performed to verify the editing plasmid. And if the result of PCR had no band, the editing plasmid may be lost. Single colony without bands from the result of PCR were inoculated into liquid mediums of RM and RM+Spe, respectively, and cultivated at 30° C. At the next day, the culture results in both media were observed to confirm that the editing plasmid had been eliminated when the colonies could grow cloudy in RM but clear in RM+Spe.

In one example for constructing the genetically modified strain of Z. mobilis, the editing plasmid was electro-transferred into ZM4 and plated onto RM+Spe. The transformants were verified with primers Chk-lrp-F (shown as SEQ ID NO:15) and Chk-lrp-R (shown as SEQ ID NO:16). And positive colonies were screened by a colony PCR with primers pEZ15A-F (SEQ ID NO:17) and pEZ15A-R (SEQ ID NO:18).

Figure 1:
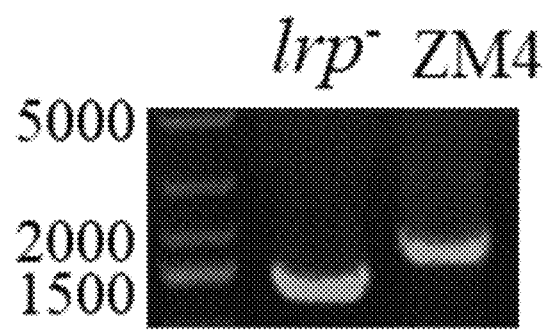
FIG. 1 illustrates the results of colony PCRs provided with embodiments.

As shown in FIG. 1, if the colony PCR does not show a band of 2000 bp but a band of 1500 bp, the result could indicate that the editing plasmid has lost in the positive colonies, and lrp⁻ has been successfully constructed.

3. Growth Test with Yeast Extract or Ammonium Sulfate as Sole N Source

RM medium (yeast extract as sole N source): 1% yeast extract, 0.2% KH₂PO₄, 50 g/L glucose; pH 5.8; sterilization at 108° C. for 30 min.

MM medium (ammonium sulfate as sole N source): 50 g/L glucose, 1 g/L KH₂PO₄, 1 g/L K₂HPO₄, 0.5 g/L NaCl, 1 g/L (NH₄)₂SO₄, sterilization at 108° C. for 30 min; 0.5 g/L MgSO₄·7H₂O, 0.025 g/L Na₂MoO₄·2H₂O, filtering to sterilize.

Growth tests of ZM4 and lrp⁻ were performed in RM and MM. Firstly, the glycerol bacteria of ZM4 and lrp⁻ were respectively inoculated into a freezing tube containing 1 mL RM. And after standing and activating in a 30° C. incubator until turbidity, the bacteria were shifted into a 100 mL triangular flask containing 80 mL of RM to be used as a seed for growth test. And the seed was subjected to standing and culturing in the 30° C. incubator. After culturing to the logarithmic growth phase (OD 600 nm value is 0.8~2), the thalli from the seed culture were collected and cleaned, and shifted into a 100 mL anaerobic bottle filled with 40 mL RM or 50 mL MM, and cultivated with an initial OD600 nm value of 0.1, at 30° C. and 100 rpm. The OD600 nm value of the bacterial solution at different time of its growth process could be tested by an ultraviolet spectrophotometer. And the test could be ended if the OD600 nm value of the bacterial solution became stable.

Figure 2A:
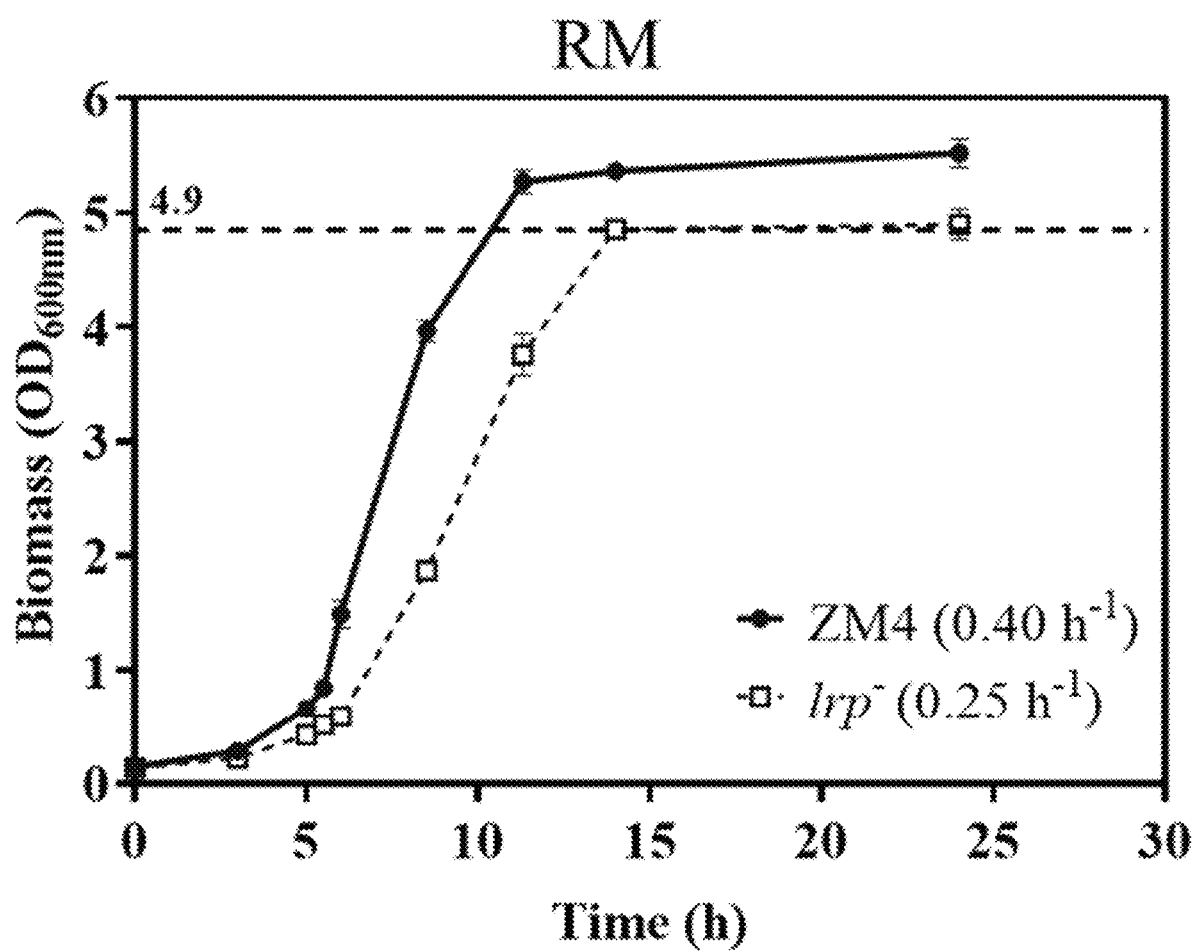
FIG. 2A illustrates growth curves of the strain of ZM4 and the strain of lrp⁻ respectively in a medium named RM provided with embodiments.
Figure 2B:
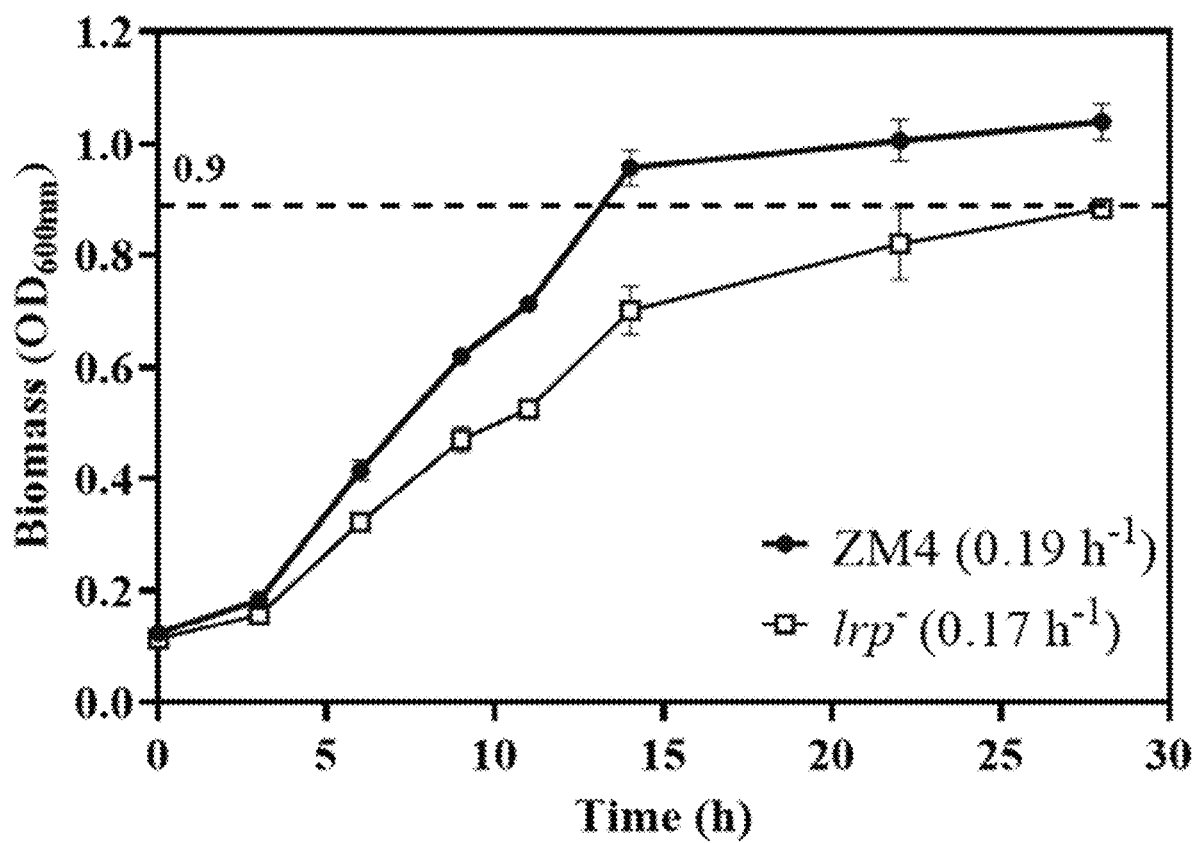
FIG. 2B illustrates growth curves of the strain of ZM4 and the strain of lrp⁻ respectively in a medium named MM provided with embodiments.

The growth curves of ZM4 and lrp$^-$ could be draw by sampling and testing OD600 nm at regular intervals in the bacterial growth process. As shown in FIG. 2, the specific growth rate and biomass of lrp$^-$ in RM and MM were both lower than ZM4.

4. Growth Test with Nitrogen Gas and Ammonium Sulfate as Mixed N Source

MMN medium (nitrogen gas and ammonium sulfate as mixed N source): the air in a anaerobic flask filled with MM medium was evacuated by means of a vacuum pump for 30 s, followed by aerating nitrogen gas for 30 s, the nitrogen gas pressure being set at 0.05 MPa, and repeated three times.

Figure 4:
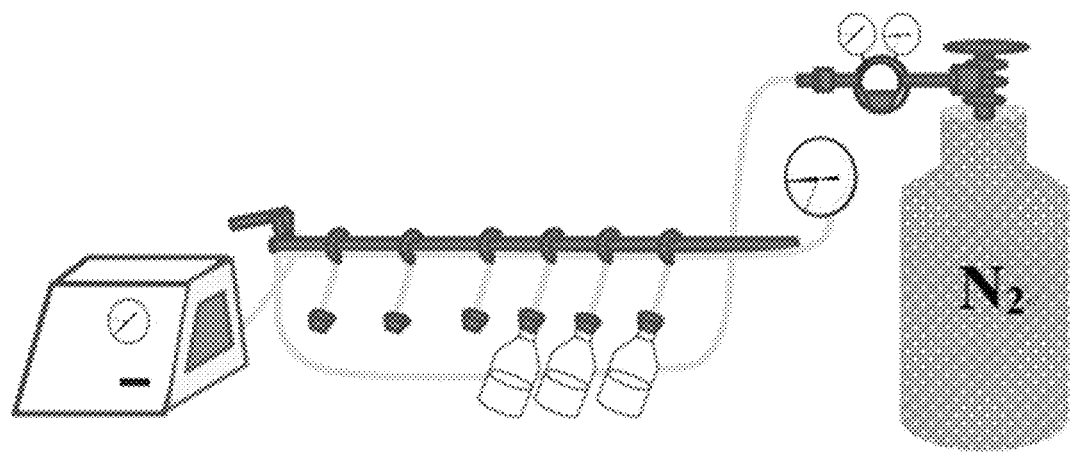
FIG. 4 illustrates a schematic diagram of the structure of the device for aerating nitrogen gas into a medium named MM, and a medium named MM-provided with embodiments.

Growth tests of ZM4 and lrp$^-$ were performed in MMN (FIG. 4 shows a schematic diagram of the structure of the device for aerating nitrogen gas). Firstly, the glycerol bacteria of ZM4 and lrp$^-$ were respectively inoculated into a freezing tube containing 1 mL of RM. And after standing and activating in a 30° C. incubator until turbidity, the bacteria were shifted into a 100 mL triangular flask containing 80 mL of RM to be used as a seed for growth test. And the seed was subjected to standing and culturing in the 30° C. incubator. After culturing to the logarithmic growth phase (OD 600 nm value is 0.8~2), the thalli from the seed culture were collected and cleaned, and shifted into a 100 mL anaerobic bottle filled with 35 mL MMN, and cultivated with an initial OD600 nm value of 0.1, 30° C., and 100 rpm. The OD600 nm value of the bacterial solution at different time of its growth process could be tested by an ultraviolet spectrophotometer. And the test could be ended if the OD600 nm value of the bacterial solution became stable.

Figure 3:
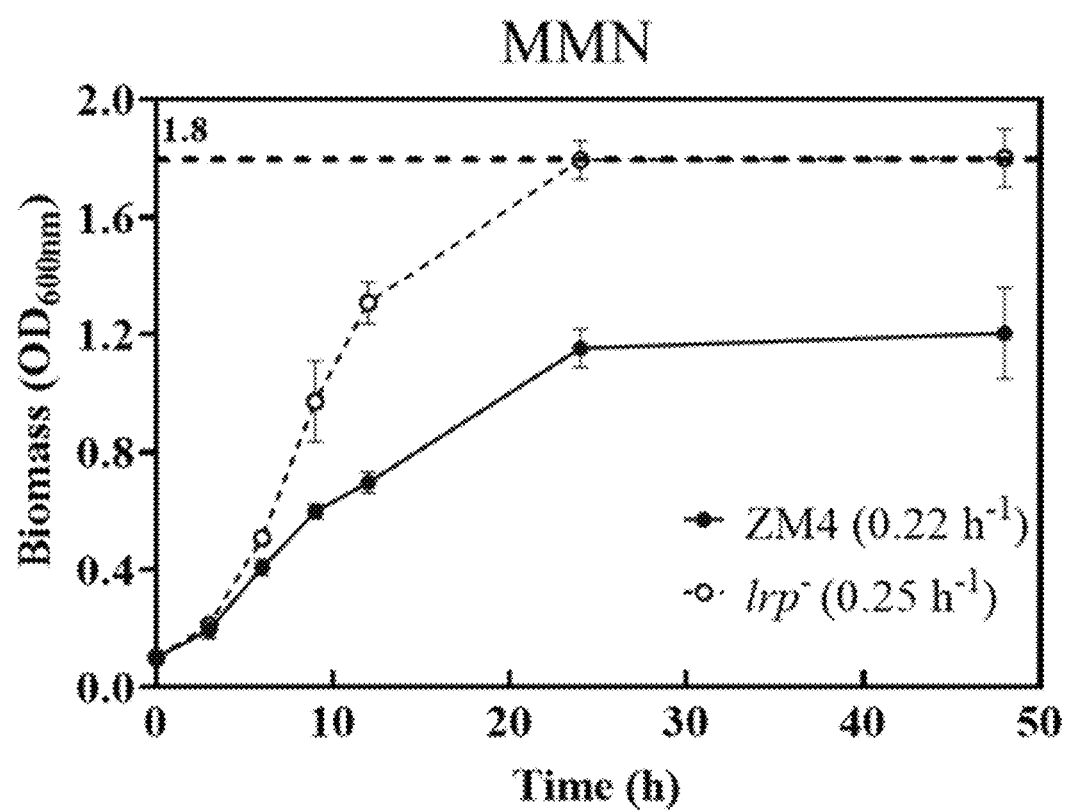
FIG. 3 illustrates growth curves of the strain of ZM4 and the strain of lrp⁻ respectively in a medium named MMN provided with embodiments.

The growth curves of ZM4 and lrp$^-$ could be draw by sampling and testing OD600 nm value at regular intervals in the bacterial growth process. As shown in FIG. 3, the specific growth rate and biomass of lrp$^-$ in MMN were both higher than ZM4.

5. Growth Test with Nitrogen Gas as Sole N Source

MM$^-$ medium (nitrogen gas as sole N source, without other N source): 50 g/L glucose, 1 g/L $KH_2PO_4$, 1 g/L $K_2HPO_4$, 0.5 g/L NaCl, and sterilizing at 108° C. for 30 min; 0.5 g/L $MgSO_4 \cdot 7H_2O$, 0.025 g/L $Na_2MoO_4 \cdot 2H_2O$, filtering to sterilize.

Growth tests of ZM4 and lrp$^-$ were performed in MM- and MM-N (FIG. 4 shows a schematic diagram of the structure of the device for aerating nitrogen gas, MM-N means nitrogen gas aeration into MM$^-$). Firstly, the glycerol bacteria of ZM4 and lrp$^-$ were respectively inoculated into a freezing tube containing 1 mL of RM. And after standing and activating in a 30° C. incubator until turbidity, the bacteria were shifted into a 100 mL triangular flask containing 80 mL of RM to be used as a seed for growth test. And the seed was subjected to standing and culturing in the 30° C. incubator. After culturing to the logarithmic growth phase (OD 600 nm is 0.8~2), the thalli from the seed culture were collected and cleaned, and shifted into a 50 mL triangular flask filled with 40 mL MM- or a 100 mL anaerobic bottle filled with 35 mL MM-N, and cultivated with a initial OD600 nm value of 0.2, 30° C., and 100 rpm. The OD600 nm value of the bacterial solution at different time of its growth process could be tested by an ultraviolet spectrophotometer. And the test could be ended if the OD600 nm value of the bacterial solution became stable.

Figure 5B:
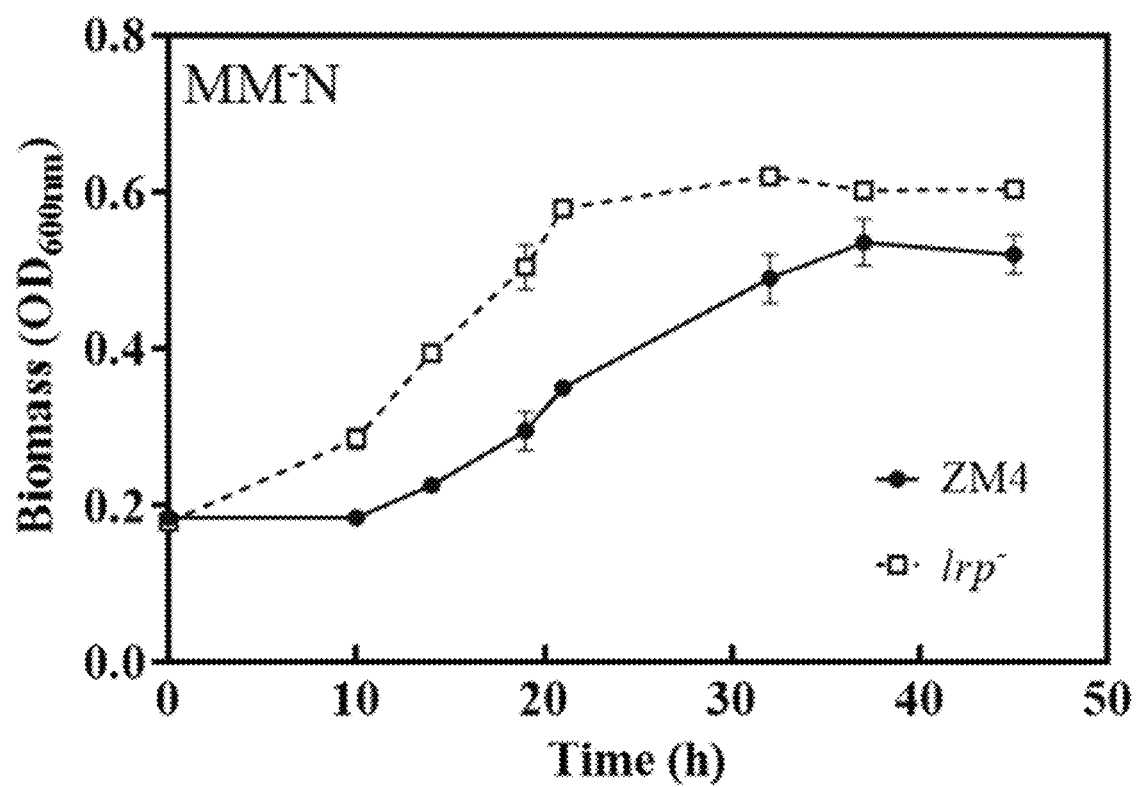
FIG. 5B illustrates growth curves of the strain of ZM4 and the strain of lrp⁻ respectively in a medium named MM-N provided with embodiments.
Figure 5C:
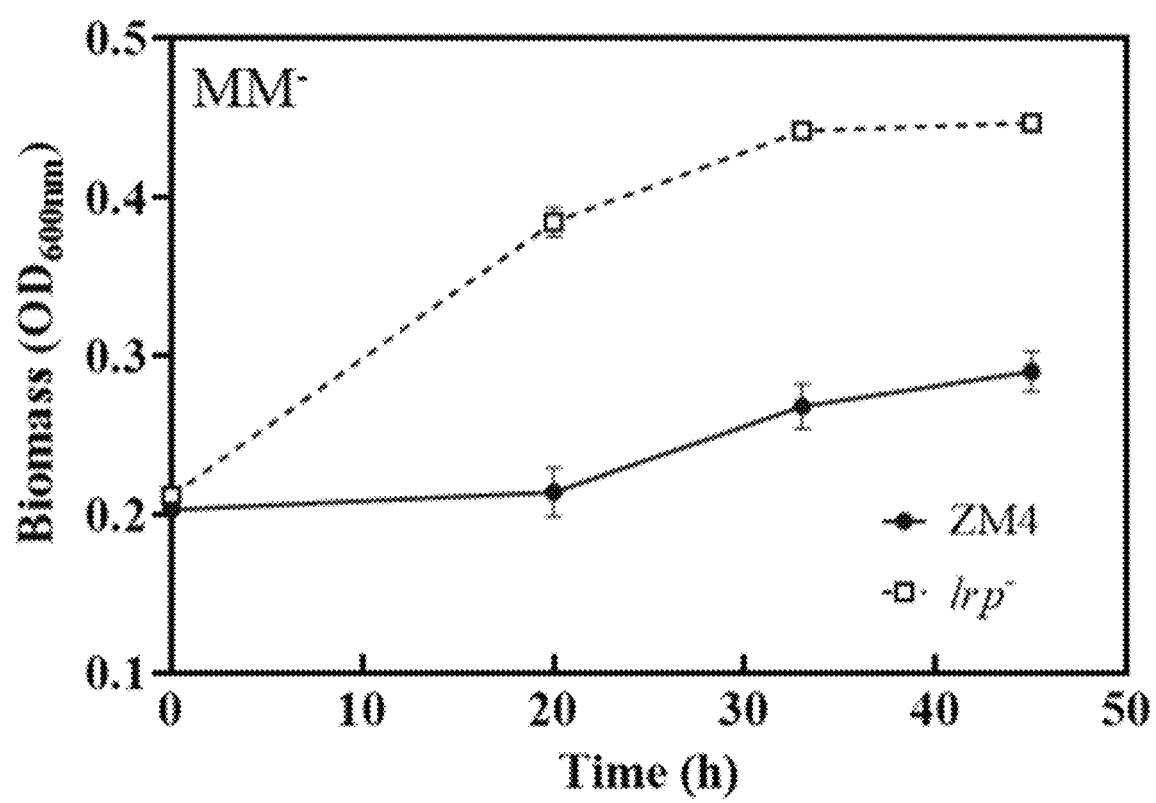
FIG. 5C illustrates growth curves of the strain of ZM4 and the strain of lrp⁻ respectively in a medium named MM⁻ provided with embodiments.
Figure 6:
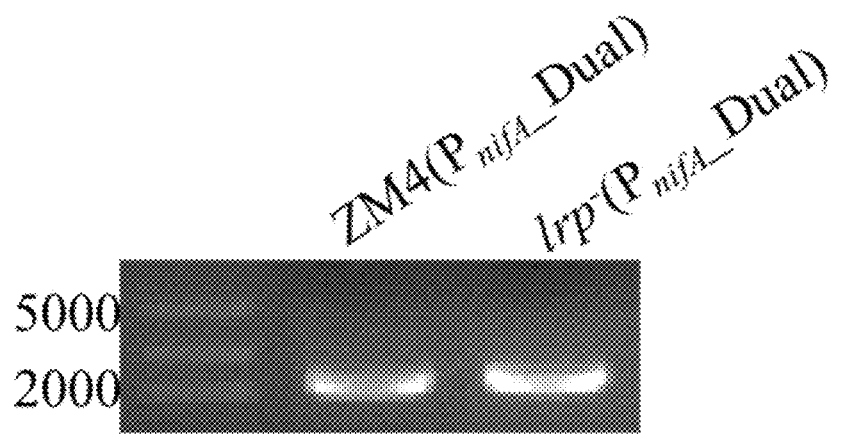
FIG. 6 illustrates the results of colony PCRs of a strain named ZM4 ($P_{nifA}$_Dual) and a strain named lrp⁻ ($P_{nifA}$_Dual) provided with embodiments. ZM4($P_{nifA}$_Dual) and lrp⁻ ($P_{nifA}$_Dual) both have a recombinant plasmid with carrying a dual fluorescence reporting system.
Figure 7A:
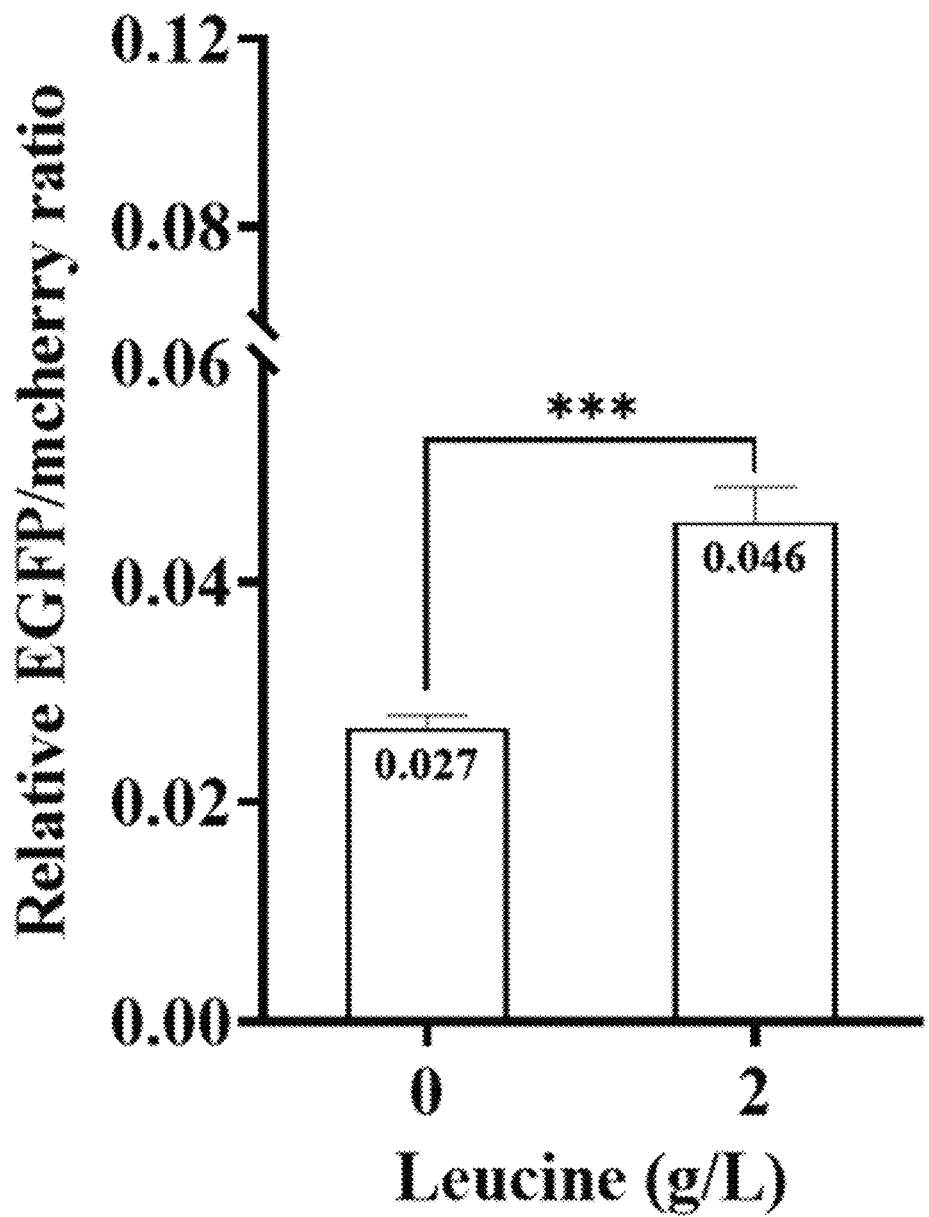
FIG. 7A illustrates the fluorescence relative ratios of EGFP/mCherry under two fermentative conditions of 0 g/L and 2 g/L leucine of a strain named ZM4($P_{nifA}$_Dual) provided with embodiments. ZM4(P$_{nifA}$_Dual) has a recombinant plasmid with carrying a dual fluorescence reporting system.
Figure 7B:
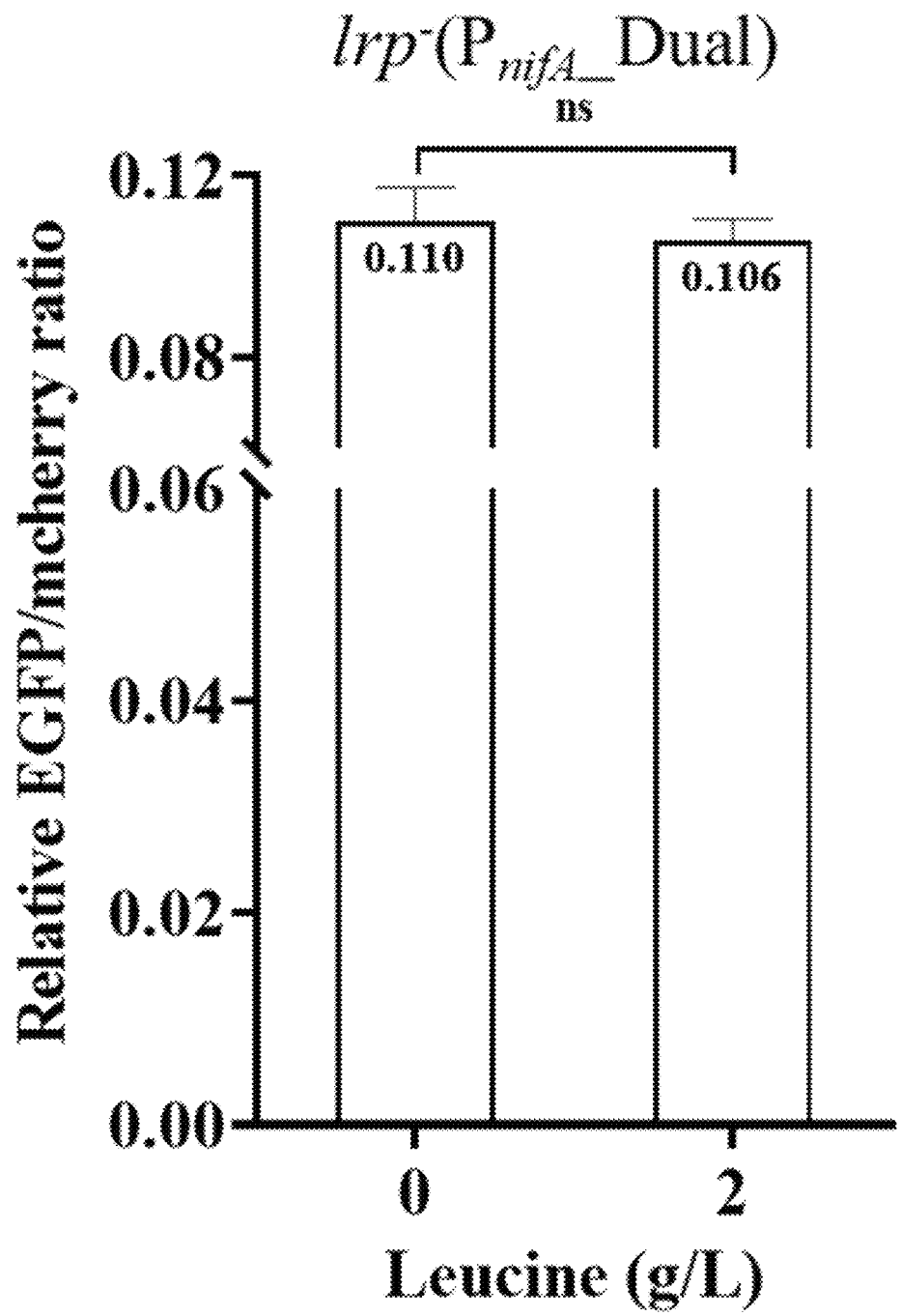
FIG. 7B illustrates the fluorescence relative ratios of EGFP/mCherry under two fermentative conditions of 0 g/L and 2 g/L leucine of a strain named lrp⁻ (P$_{nifA}$_Dual) provided with embodiments. lrp⁻ (P$_{nifA}$_Dual) has a recombinant plasmid with carrying a dual fluorescence reporting system.

The growth curves of ZM4 and lrp$^-$ could be draw by sampling and testing OD600 nm at regular intervals in the bacterial growth process. As shown in FIG. 5, the specific growth rate and biomass of lrp$^-$ in MM$^-$N or MM$^-$ were both higher than ZM4.

In addition, embodiments disclose a gene of regulating nitrogen metabolism from Z. mobilis. Therein, the said gene encodes feast/famine response regulating protein or leucine response regulating protein Lrp. The gene locates at ZMO1107 site of genome of a ZM4's genome. The protein of Lrp could inhibit the expression of the gene of nifA for regulating N fixation.

In some embodiments, differentially expressed genes between ZM4 and lrp$^-$ could be mined by RNA-Seq. Specifically, ZM4 and lrp$^-$ were inoculated in RM with a 80% bottling amount of a 50 mL triangular flask at 30° C. and 100 rpm. When the bacteria solution of ZM4 or lrp$^-$ were grown in RM and MM to the OD600 nm value of 0.4~0.6, 10 mL of thalli from the culture were collected by centrifugation at 4000 rpm, and immediately stored in a –80° C. refrigerator after liquid nitrogen flash freezing. Finally, the collected thalli of ZM4 and lrp$^-$ were performed RNA-Seq by GENEWIZ (Suzhou, China) to obtain differentially expressed genes between ZM4 and lrp$^-$, as shown in table 3. These genes include the gene of nifA for regulating N fixation and the other genes for N fixation. And the result suggest that Lrp may regulate the biological N fixation process of Z. mobilis.

TABLE 3 differentially expressed genes between ZM4 and lrp$^-$ in RM and MM

| Locus ID | Gene | Product | Fold change MM | Fold change RM |
|---|---|---|---|---|
| ZMO1107 | lrp | Transcriptional regulator Lrp | 826.00 | 7912.95 |
| ZMO1815 | — | TonB-dependent siderophore receptor | 26.71 | 308.44 |
| ZMO0095 | — | Hypothetical protein | 20.32 | 86.05 |
| ZMO1838 | — | TOBE domain protein | 15.64 | 27.08 |
| ZMO1848 | — | Iron ABC transporter permease | 14.21 | 74.01 |
| ZMO1816 | nifA | Nif-specific transcriptional activator NifA | 12.31 | 68.30 |
| ZMO1823 | nifH | Nitrogenase reductase iron protein | 11.82 | 541.54 |
| ZMO1825 | nifK | Nitrogenase molybdenum-iron protein beta chain | 11.82 | 159.58 |
| ZMO1298 | — | TonB-dependent receptor plug domain | 10.24 | 26.39 |
| ZMO1824 | nifD | Nitrogenase molybdenum-iron protein alpha chain | 9.89 | 629.04 |
| ZMO1837 | modD | ModD protein | 9.54 | 21.41 |
| ZMO1847 | — | ABC transporter permease | 9.49 | 33.50 |
| ZMO1832 | iscA | Iron-sulfur cluster assembly accessory protein | 9.44 | 200.28 |
| ZMO1834 | nifS2 | Cysteine desulfurase NifS | 8.80 | 21.81 |
| ZMO1846 | — | ABC transporter related protein | 8.42 | 9.57 |
| ZMO1827 | nifN | Nitrogenase cofactor biosynthesis NifN | 7.84 | 41.55 |
| ZMO0560 | hisC3 | Histidinol-phosphate aminotransferase HisC | 6.91 | 56.45 |
| ZMO1826 | nifE | Nitrogenase cofactor biosynthesis NifE | 6.31 | 60.04 |
| ZMO0992 | — | Peptidase S10 serine carboxypeptidase | 6.06 | 34.98 |
| ZMO1828 | nifX | Nitrogen gas fixation protein NifX | 6.04 | 32.21 |
| ZMO1835 | nifV | Homocitrate synthase | 5.90 | 11.00 |

TABLE 3-continued differentially expressed genes between ZM4 and lrp− in RM and MM

| Locus ID | Gene | Product | Fold change MM | Fold change RM |
|---|---|---|---|---|
| ZMO0412 | — | Multiple antibiotic resistance protein | 5.51 | 6.44 |
| ZMO1841 | rseC | Positive regulator of sigma E RseC | 5.39 | 4.28 |
| ZMO0087 | — | Hypothetical protein | 5.30 | 13.18 |
| ZMO1008 | glcD | Glycolate oxidase subunit GlcD | 5.05 | 12.23 |
| ZMO0301 | — | PepSY-associated TM helix domain protein | 4.90 | 10.86 |
| ZMO1672 | — | Hypothetical protein | 4.29 | 2.10 |
| ZMO1842 | apbE | ApbE family lipoprotein | 4.11 | 4.89 |
| ZMO1817 | nifB | Nitrogenase cofactor biosynthesis protein NifB | 4.09 | 35.81 |
| ZMO0026 | — | Sel1 domain protein repeat-containing protein | 3.98 | 6.92 |
| ZMO1820 | fixU | Nitrogen fixation protein FixT/FixU | 3.87 | 5.11 |
| ZMO1378 | eutP | Ethanolamine transporter | 3.81 | 11.33 |
| ZMO1380 | — | AraC family transcriptional regulator | 3.78 | 13.28 |
| ZMO1831 | nifQ | NifQ family protein | 3.74 | 19.17 |
| ZMO0302 | — | Aryl-sulfate sulfotransferase | 3.51 | 2.86 |
| ZMO0914 | folD | Bifunctional methylenetetrahydrofolate | 3.22 | 3.51 |
| ZMO1732 | ahpC | Alkyl hydroperoxide reductase | 3.12 | 2.42 |
| ZMO1829 | — | Nitrogen fixation protein | 2.98 | 36.77 |
| ZMO1009 | — | SapC family protein | 2.95 | 3.88 |
| ZMO1377 | — | Hypothetical protein | 2.87 | 2.10 |
| ZMO1819 | nifZ | NifZ family protein | 2.82 | 4.20 |
| ZMO1139 | ilvI | Acetolactate synthase large subunit | 2.82 | 3.63 |
| ZMO1836 | nifW | Nitrogen fixation protein NifW | 2.82 | 2.85 |
| ZMO0223 | — | Auto-transporter adhesin head GIN domain | 2.81 | 7.43 |
| ZMO0889 | mro | Aldose 1-epimerase | 2.63 | 4.71 |
| ZMO1840 | — | Isochorismatase hydrolase | 2.55 | 2.66 |
| ZMO0085 | mcp | Methyl-accepting chemotaxis sensory transducer | 2.54 | 2.03 |
| ZMO0422 | — | BadM/Rrf2 family transcriptional regulator | 2.50 | 3.39 |
| ZMO1527 | acrB | Multidrug efflux pump subunit AcrB | 2.48 | 2.60 |
| ZMO1787 | — | Hypothetical protein | 2.46 | 9.18 |
| ZMO1528 | acrB | Multidrug efflux pump subunit AcrB | 2.46 | 2.92 |
| ZMO0069 | — | Major tail tube protein | 2.43 | 13.27 |
| ZMO1140 | ilvH | Acetolactate synthase small subunit | 2.40 | 3.49 |
| ZMO0492 | glnB | Nitrogen regulatory protein PII | 2.33 | 3.13 |
| ZMO1138 | miaA | TRNA dimethylallyltransferase MiaA | 2.25 | 2.53 |
| ZMO1586 | bfr2 | Bacterioferritin | 2.25 | 5.52 |
| ZMO1040 | — | TonB-dependent receptor | 2.22 | 3.83 |
| ZMO1529 | acrA | Multidrug efflux pump subunit AcrA | 2.17 | 3.53 |
| ZMO0543 | acnA | Aconitate hydratase | 2.15 | 2.86 |
| ZMO1775 | — | Hypothetical protein | 2.11 | 2.26 |
| ZMO1525 | tolC | Multidrug efflux pump subunit TolC | 2.05 | 2.18 |
| ZMO0970 | — | Purine nucleoside permease | −2.02 | −2.28 |
| pZYM36_047 | — | Phage tail protein X-like | −2.04 | 2.76 |
| ZMO0610 | flgF | Flagellar basal-body rod protein FlgF | −2.04 | −2.41 |
| ZMO0635 | fliG | Flagellar motor switch protein FliG | −2.07 | −2.32 |
| ZMO0969 | — | Xanthine/uracil/vitamin C permease | −2.09 | −2.25 |
| ZMO0145 | — | Peptidase M28 | −2.09 | −2.01 |
| ZMO1681 | — | Aspartate-alanine antiporter | −2.13 | −9.34 |
| ZMO0627 | — | GT2 family glycosyltransferase | −2.28 | −2.31 |
| ZMO0614 | flgB | Flagellar basal-body rod protein FlgB | −2.31 | −2.70 |
| ZMO0634 | fliF | Flagellar M-ring protein FliF | −2.33 | −2.61 |
| ZMO0628 | — | Glycosyl transferase family 2 | −2.51 | −2.21 |
| ZMO0611 | flgE | Flagellar hook protein FlgE | −2.62 | −2.42 |
| ZMO1632 | dapE | Succinyl-diaminopimelate desuccinylase | −2.65 | −2.62 |
| ZMO0636 | fliH | Negative regulator of FliI ATPase | −2.78 | −2.64 |
| ZMO0202 | mcpA | Methyl-accepting chemotaxis sensory transducer | −2.82 | −3.60 |
| ZMO1700 | — | Hypothetical protein | −2.90 | −2.09 |
| ZMO1684 | serC | Phosphoserine aminotransferase | −3.10 | −2.30 |
| ZMO0131 | — | Metallophosphoesterase | −3.11 | −2.22 |
| ZMO0613 | flgC | Flagellar basal-body rod protein FlgC | −3.19 | −2.40 |
| ZMO1470 | — | Transglycosylase domain-containing protein | −3.27 | −4.49 |
| ZMO1522 | — | TonB-dependent receptor | −4.28 | 5.56 |
| ZMO1976 | — | Hypothetical protein | −7.34 | −11.61 |

The above is only the preferred embodiments of this disclosure and is not intended to limit this disclosure. Any modification, equivalent replacement, improvement, etc., made within the spirit and principle of this disclosure shall be included in the scope of this disclosure.

What is claimed is:

1. A genetically modified strain of *Zymomonas mobilis* having a modified genome from a *Z. mobilis* subsp. *mobilis* ZM4(ATCC 31821) strain by knocking out a ZMO1107 loci having gene ID 58026885.

\* \* \* \* \*

SEQUENCE LISTING

```
Sequence total quantity: 20
SEQ ID NO: 1                moltype = DNA   length = 148
FEATURE                     Location/Qualifiers
source                      1..148
                            mol_type = other DNA
                            organism = unidentified
SEQUENCE: 1
tttgaccctt tatttgaccc tctttttttg gcatgtaaaa aaatccttta aaatcaatag    60
gttaaaaata ggctctatt ttagggttat ttggctattt ttgcccgata ttcctttcat   120
ttaggggat ttttaattat ttactcta                                      148

SEQ ID NO: 2                moltype = DNA   length = 28
FEATURE                     Location/Qualifiers
source                      1..28
                            mol_type = other DNA
                            organism = unidentified
SEQUENCE: 2
gttcactgcc gcacaggcag cttagaaa                                      28

SEQ ID NO: 3                moltype = DNA   length = 1269
FEATURE                     Location/Qualifiers
source                      1..1269
                            mol_type = other DNA
                            organism = unidentified
```

```
SEQUENCE: 3
ccaatccatt cagcgacatc tagccgaact gagctgatga caggcattgc gattagggca    60
atatcacagg caaaatattg caccagtaac ggcggaatat ggcgtccagc taaggtttcg   120
gcggtatcaa gacggatgtt ggtaggcact tcgcgcgtta agtccattaa acgctgatag   180
gcatttttta acaaatgagg gtcatgttgc cccttatctt gggcgataca atctactaat   240
tgccgccaga cagcgatctt ttccgcttcc gtgttaaggg gctgatccat aattgtttga   300
agcatatcgt cgaaacgcac gcctgattcc cgattttag tgaataccctt gcgcattatc   360
ggtaaaggca agtggttaac atatcgctga catttgccat atttgggaga aaaactggaa   420
gatattaaaa aatattttt acatggggta atttattctt ttttttctga gagatgtttt   480
ttttatcaga ttttacccca tttaattatc aagtcatcga attgaggctt ttttttacat   540
aatcgtgcat aagtgaagtt gtatttttcg gcaatttat tatctagccg gaagattaaa   600
tagaaggact aagtccgtga cggctaatta cccactctgt tgataccaaa gagtaatccc   660
ccccattctt ccgatatgtt tagaaaagaa tatattattt tttgaatgat caaggcactg   720
gcgatcatga atatttctga aatcttttca ggtctatatc ggttgccggt gtgccttctt   780
cggaagaaat gacaaaatat ctgaacagcg gcttcgctgt tttttttgtc aaaaaaaacg   840
ggctgagttt ttcagcccgt ttttctttgt ctaaattcaa tgcttaagat caggccgccg   900
gagtagcgac atgggtatcg gcatagattg accagaattg cgcgatcgga gcgcgactac   960
cctgaaccgt ggccaaggtg gctttggctg catcctttg acccgcaagc gcctgcgcca  1020
tacctaaacg caaagtggta aggtcattgt caacaccgga tttgctcttg caatggtga  1080
agagattgat cgcaaggctg taatcacccg cacccaaggc caaagtacca tcagtgaagg  1140
catctttgcc agtagcggct ttactgtcac gagcaacagc cttggcaaga tcggttttt   1200
cagccgccac tttcaggcga gcggtggaaa gccatttgct gaccgtggtg tccgttgcac  1260
tgagaactt                                                         1269

SEQ ID NO: 4         moltype = DNA  length = 32
FEATURE              Location/Qualifiers
source               1..32
                     mol_type = other DNA
                     organism = unidentified
SEQUENCE: 4
acttgattca atcgatcgtc tgattcttga ga                                 32

SEQ ID NO: 5         moltype = DNA  length = 36
FEATURE              Location/Qualifiers
source               1..36
                     mol_type = other DNA
                     organism = synthetic construct
SEQUENCE: 5
gaaaacttga ttcaatcgat cgtctgattc ttgaga                             36

SEQ ID NO: 6         moltype = DNA  length = 36
FEATURE              Location/Qualifiers
source               1..36
                     mol_type = other DNA
                     organism = synthetic construct
SEQUENCE: 6
gaactctcaa gaatcagacg atcgattgaa tcaagt                             36

SEQ ID NO: 7         moltype = DNA  length = 636
FEATURE              Location/Qualifiers
source               1..636
                     mol_type = other DNA
                     organism = unidentified
SEQUENCE: 7
ccaatccatt cagcgacatc tagccgaact gagctgatga caggcattgc gattagggca    60
atatcacagg caaaatattg caccagtaac ggcggaatat ggcgtccagc taaggtttcg   120
gcggtatcaa gacggatgtt ggtaggcact tcgcgcgtta agtccattaa acgctgatag   180
gcatttttta acaaatgagg gtcatgttgc cccttatctt gggcgataca atctactaat   240
tgccgccaga cagcgatctt ttccgcttcc gtgttaaggg gctgatccat aattgtttga   300
agcatatcgt cgaaacgcac gcctgattcc cgattttag tgaataccctt gcgcattatc   360
ggtaaaggca agtggttaac atatcgctga catttgccat atttgggaga aaaactggaa   420
gatattaaaa aatattttt acatggggta atttattctt ttttttctga gagatgtttt   480
ttttatcaga ttttacccca tttaattatc aagtcatcga attgaggctt ttttttacat   540
aatcgtgcat aagtgaagtt gtatttttcg gcaatttat tatctagccg gaagattaaa   600
tagaaggact aagtccgtga cggctaatta cccact                            636

SEQ ID NO: 8         moltype = DNA  length = 38
FEATURE              Location/Qualifiers
source               1..38
                     mol_type = other DNA
                     organism = synthetic construct
SEQUENCE: 8
gtcaccagct caccgtctcc aatccattca gcgacatc                           38

SEQ ID NO: 9         moltype = DNA  length = 43
FEATURE              Location/Qualifiers
source               1..43
                     mol_type = other DNA
                     organism = synthetic construct
```

-continued

```
SEQUENCE: 9
ggattactct ttggtatcaa cagagtgggt aattagccgt cac                    43

SEQ ID NO: 10           moltype = DNA  length = 633
FEATURE                 Location/Qualifiers
source                  1..633
                        mol_type = other DNA
                        organism = unidentified
SEQUENCE: 10
ctgttgatac caaagagtaa tccccccat tcttccgata tgtttagaaa agaatatatt    60
atttttgaa tgatcaaggc actggcgatc atgaatattt ctgaaatctt ttcaggtcta   120
tatcggttgc cggtgtgcct tcttcggaag aaatgacaaa atatctgaac agcggcttcg  180
ctgttttttt tgtcaaaaaa acgggctga gttttcagc ccgttttct ttgtctaaat     240
tcaatgctta agatcaggcc gccggagtag cgacatgggt atcggcatag attgaccaga  300
attgcgcgat cggagcgcga ctaccctgaa ccgtggccaa ggtggctttg gctgcatcct  360
tttgacccgc aagcgcctgc gccataccta aacgcaaagt ggtaaggtca ttgtcaacac  420
cggatttgct cttggcaatg gtgaagagat tgatcgcaag gctgtaatca cccgcaccca  480
aggccaaagt accatcagtg aaggcatctt tgccagtgca ggctttactg tcacgagcaa  540
cagccttggc aagatcggct ttttcagccg ccactttcag gcgagcggtg aaagccatt   600
tgctgaccgt ggtgtccgtt gcactgagaa ctt                               633

SEQ ID NO: 11           moltype = DNA  length = 24
FEATURE                 Location/Qualifiers
source                  1..24
                        mol_type = other DNA
                        organism = synthetic construct
SEQUENCE: 11
ctgttgatac caaagagtaa tccc                                         24

SEQ ID NO: 12           moltype = DNA  length = 37
FEATURE                 Location/Qualifiers
source                  1..37
                        mol_type = other DNA
                        organism = synthetic construct
SEQUENCE: 12
tcgagatctg atatcactaa gttctcagtg caacgga                           37

SEQ ID NO: 13           moltype = DNA  length = 31
FEATURE                 Location/Qualifiers
source                  1..31
                        mol_type = other DNA
                        organism = synthetic construct
SEQUENCE: 13
agtgatatca gatctcgagc tcggtacccg g                                 31

SEQ ID NO: 14           moltype = DNA  length = 20
FEATURE                 Location/Qualifiers
source                  1..20
                        mol_type = other DNA
                        organism = synthetic construct
SEQUENCE: 14
agacggtgag ctggtgacct                                              20

SEQ ID NO: 15           moltype = DNA  length = 20
FEATURE                 Location/Qualifiers
source                  1..20
                        mol_type = other DNA
                        organism = synthetic construct
SEQUENCE: 15
gtcgccaagg ctatccaaag                                              20

SEQ ID NO: 16           moltype = DNA  length = 20
FEATURE                 Location/Qualifiers
source                  1..20
                        mol_type = other DNA
                        organism = synthetic construct
SEQUENCE: 16
tgtgggagcc ttaagtgcag                                              20

SEQ ID NO: 17           moltype = DNA  length = 22
FEATURE                 Location/Qualifiers
source                  1..22
                        mol_type = other DNA
                        organism = synthetic construct
SEQUENCE: 17
ggcaaagcca ccctattttt ag                                           22

SEQ ID NO: 18           moltype = DNA  length = 20
FEATURE                 Location/Qualifiers
```

```
source                  1..20
                        mol_type = other DNA
                        organism = synthetic construct
SEQUENCE: 18
cacttcactg acaccctcat                                                     20

SEQ ID NO: 19           moltype = DNA  length = 914
FEATURE                 Location/Qualifiers
source                  1..914
                        mol_type = other DNA
                        organism = unidentified
SEQUENCE: 19
gcgctagcgg agtgtatact ggcttactat gttggcactg atgagggtgt cagtgaagtg          60
cttcatgtgg caggagaaaa aaggctgcac cggtgcgtca gcagaatatg tgatacagga         120
tatattccgc ttcctcgctc actgactcgc tacgctcggt cgttcgactg cggcgagcgg         180
aaatggctta cgaacggggc ggagatttcc tggaagatgc caggaagata cttaacaggg         240
aagtgagagg gccgcggcaa agccgttttt ccataggctc cgccccctg acaagcatca          300
cgaaatctga cgctcaaatc agtggtggcg aaacccgaca ggactataaa gataccaggc         360
gtttccccct ggcggctccc tcgtgcgctc tcctgttcct gcctttcggt ttaccggtgt         420
cattccgctg ttatggccgc gtttgtctca ttccacgcct gacactcagt tccgggtagg         480
cagttcgctc caagctggac tgtatgcacg aaccccccgt tcagtccgac cgctgcgcct         540
tatccggtaa ctatcgtctt gagtccaacc cggaaagaca tgcaaaagca ccactggcag         600
cagccactgg taattgattt agaggagtta gtcttgaagt catgcgccgg ttaaggctaa         660
actgaaagga caagttttgg tgactgcgct cctccaagcc agttacctcg gttcaaagag         720
ttggtagctc agagaacctt cgaaaaaccg ccctgcaagg cggttttttc gttttcagag         780
caagagatta cgcgcagacc aaaacgatct caagaagatc atcttattaa tcagataaaa         840
tatttcttga tttcagtgca atttatctct tcaaatgtag cacctgaagt cagccccata         900
cgatataagt tgta                                                           914

SEQ ID NO: 20           moltype = DNA  length = 874
FEATURE                 Location/Qualifiers
source                  1..874
                        mol_type = other DNA
                        organism = unidentified
SEQUENCE: 20
acggtgagct ggtgacctgc cttatctctt tccccagtag ctaaaaatag ggtggctttg          60
cccgtgtata taaccaacag ctttctcatg gttttttccga ggcaggattc aacgaatttc        120
cccactagga agaactaaga aagggaatcg tgaaaatatc cctaaaatag ggaagtcgat         180
tttcagaatc tgtgaagggg tctatcaata ttgattaaac cgtctatcaa aaaaaggggt         240
aaaattgata gaccttgcct cattcgatga ataggtataa tcaaaaaatg tggttttttt         300
gattaaaggt ttatcaaata tggcgacaaa attgagaaag cagccaatca gatatgacga         360
gaatcctttc atcgaaggta tggttgtgcc agttaaaagt cagagggttc agttatctcg         420
attaggacga gatgataaca ttctggtcaa tcaagccact ggtgagatgc aaggcactca         480
tgtgacgact tacagacgtg ttgatagtga agaatttgta aaattattta gcaccaatat         540
cgcgctaact tttgaactag gagccgctgg aataaaagct ttcagcgttc tggtttggat         600
acttcaagac aaaggcatca gcaaagacct cgtccctta gacaaattcg ttttagagga         660
ctttcttaac gcacaagaaa aaaaactggc actatctcaa gctaccttg caagaggtct          720
agccgaatta gaaaaagcta aaatcattgc aaagcatgtt cgccaaggat ggtattttat         780
taatcctaat ttcgttttca atggcgaccg cgtagctttc acaacagtta tagaacgcaa         840
aaagacgctc caaaagcaag acgaatcaga ataa                                     874
```